United States Patent
Eissa et al.

(10) Patent No.: US 11,035,817 B1
(45) Date of Patent: Jun. 15, 2021

(54) METHOD AND PROCESS TO MAKE AND USE COTTON-TIPPED ELECTROCHEMICAL IMMUNOSENSOR FOR THE DETECTION OF CORONA VIRUS

(71) Applicant: Alfaisal University, Riyadh (SA)

(72) Inventors: Shimaa Eissa, Riyadh (SA); Mohammed Zourob, Riyadh (SA)

(73) Assignee: Alfaisal University, Riyadh (SA)

( * ) Notice: Subject to any disclaimer, the term of this patent is extended or adjusted under 35 U.S.C. 154(b) by 0 days.

(21) Appl. No.: 17/092,460

(22) Filed: Nov. 9, 2020

(51) Int. Cl.
*G01N 27/327* (2006.01)
*G01N 33/569* (2006.01)
*G01N 33/543* (2006.01)

(52) U.S. Cl.
CPC ....... *G01N 27/327* (2013.01); *G01N 33/5438* (2013.01); *G01N 33/56983* (2013.01)

(58) Field of Classification Search
CPC ........... G01N 27/327; G01N 33/56983; G01N 33/5438
See application file for complete search history.

(56) References Cited

PUBLICATIONS

Yanez-Sedeno, "Integrated Affinity Biosensing Platforms on Screen-Printed Electrodes Electrografted with Diazonium Salts" Sensors 2018, 18, 675, pp. 1-21 (Year: 2018).*

Layqah et al.,"An electrochemical immunosensor for the corona virus associated with the Middle East respiratory syndrome using an array of gold nanoparticle-modified carbon electrodes" Microchimica Acta (2019) 186: 224; pp. 1-10 (Year: 2019).*

Alamer "Rapid colorimetric lactoferrin-based sandwich immunoassay on cotton swabs for the detection of foodborne pathogenic bacteria" Taianta 185 (2018) 275-280 (Year: 2020).*

* cited by examiner

*Primary Examiner* — Dennis White
(74) *Attorney, Agent, or Firm* — Geeta Kadambi; Riddhi IP LLC

(57) ABSTRACT

A method and process to make and use cotton-tipped electrochemical immunosensor for the detection of corona viruses is described. The immunosensor were fabricated by immobilizing the virus antigens on carbon nanofiber-modified screen printed electrodes which were functionalized by diazonium electrografting and activated by EDC/NHS chemistry. The detection of virus antigens were achieved via swabbing followed by competitive assay using fixed amount of antibody in the solution. Ferro/ferricyanide redox probe was used for the detection using square wave voltammetric technique. The limits of detection for our electrochemical biosensors were 0.8 and 0.09 pg/ml for SARS-CoV-2 and MERS-CoV, respectively indicating very good sensitivity for the sensors. Both biosensors did not show significant cross reactivity with other virus antigens such as influenza A and HCoV, indicating the high selectivity of the method.

13 Claims, 10 Drawing Sheets

FIG. 4

METHOD AND PROCESS TO MAKE AND USE COTTON-TIPPED ELECTROCHEMICAL IMMUNOSENSOR FOR THE DETECTION OF CORONA VIRUS

FILED OF TECHNOLOGY

A method and process to make and use cotton-tipped electrochemical immunosensor for the detection of corona viruses is described.

BACKGROUND

The newly identified severe acute respiratory syndrome coronavirus 2 (SARS-CoV-2) is the last discovered member of the corona viruses that cause serious human respiratory infections. Other types of corona viruses were previously known such as the Middle East respiratory syndrome coronavirus (MERS-CoV), SARS-CoV1, HCoV-OC43, HCoV-229E, HCoV HKU1 and HCoV NL63. Since its first identification in China in 2019 until present, SARS-CoV-2 has spread globally causing significant morbidity and mortality. COVID-19; the disease caused by SARS-CoV-2; was declared as pandemic by the world health organization on March 2020. Until now, there are no available vaccines or drugs proven to treat COVID 19. Therefore, the timely detection of SARS-CoV-2, is urgently needed to effectively control the rapid spread of the infection.

The testing of the virus can be achieved by reverse transcription polymerase chain reaction (RT-PCR) test, detection of antigens, or by serological testing (the detection of the virus antibody). However, the serological tests are not reliable for the early diagnosis of SARS-CoV-2 infection due to the relatively long delay between infection and seroconversion. Molecular diagnosis using RT-PCR is the primary used method for the detection of corona viruses. However, PCR takes relatively long time for analysis (minimum of 3 hours), and requires several steps including the collection of the specimens by swabbing, the transport of the sample into a solution and extraction of the viral RNA before amplification. Moreover, RT-PCR is relatively expensive which hindered its wide applicability for population scale diagnosis of SARS-CoV-2, particularly in low and middle income countries. Thus, sensitive, rapid and accurate diagnostic methods based on the direct detection of the viral antigens without pretreatment is highly demanded to control the COVID 19 outbreak. There are four main structural antigens for corona viruses: nucleocapsid (N), spike (S), matrix (M), and envelope (E). Among them, the S and N proteins have the potential to be used as biomarkers because they can distinguish different types of corona viruses.

Several diagnostic methods are being developed for the detection of COVID 19. Biosensors have been widely used for many diagnostic applications showing fast, easy and reliable detection. Until now, only few biosensors have been developed for SARS-CoV-2 such as the graphene-based field-effect transistor (FET) biosensor reported by Seo. et al. The FET immunosensor was used for the detection of SARS-CoV-2 using spike 51 protein as biomarker. Plasmonic photothermal biosensors for SARS-CoV-2 through nucleic acid hybridization have been also developed. Half-strip lateral flow assays (LFA) for the detection of N protein was reported. However, LFA provide qualitative or semi-quantitative results and more work is still required to develop more accurate detection methods.

Electrochemical biosensors are one of the most popular types of biosensors which offer several advantages such as the low cost, capability of miniaturization, high sensitivity and selectivity. These advantages make them ideal for use as point-of-care devices for diagnostic applications. Electrochemical biosensors have been widely integrated with carbon nanostructures to fabricate highly sensitive devices. Carbon nanofiber (CNF) is one of the materials that showed excellent applications in biosensors because of its large surface area, stability and ease of functionalization.

Cotton swabs have been recently used in the fabrication of immunoassays for the detection of different pathogens. In these assays, the colorimetric detection was achieved based on visual discrimination of the color change. These assays are simple, fast and easy to perform. However, they only give qualitative or semi-quantitative results. Thus, more accurate methods are still required.

SUMMARY

In the instant disclosure, a novel method and process to make and use cotton-tipped electrochemical immunosensor for the detection of corona virus is described. In one embodiment a rapid test for severe acute respiratory syndrome coronavirus 2 (SARS-CoV-2) is described. In another embodiment, a process using a cotton-tipped electrochemical immunosensor using square wave voltammetry for detecting corona virus is described. In another embodiment, a mammalian is tested by swabbing nasal cavity, oral cavity or any other bodily fluid and or mucous membrane is described.

In one embodiment, a cotton-tipped electrochemical immunosensor for the detection of corona virus antigens is described. In another embodiment, a process and method of integrating the sample collection and detection tools into a single platform by coating screen printed electrodes with absorbing cotton padding is described. The immunosensor was fabricated by immobilizing the virus antigen on carbon nanofiber-modified screen printed electrodes which were functionalized by diazonium electrografting and activated by EDC/NHS chemistry. The detection of virus antigens were achieved via swabbing followed by competitive assay using fixed amount of antibody in the solution. Ferro/ferricyanide redox probe was used for the detection using square wave voltammetric technique. The limits of detection for our electrochemical biosensors were 0.8 and 0.09 pg/ml for SARS-CoV-2 and MERS-CoV, respectively indicating very good sensitivity for the sensors. Both biosensors did not show significant cross reactivity with other virus antigens such as influenza A and HCoV, indicating the high selectivity of the method. In one embodiment, the biosensor was successfully applied for the detecting of the virus antigens in spiked nasal samples showing excellent recovery percentages. In one embodiment, the electrochemical immunosensor is a diagnostic tool for the direct rapid detection of the corona viruses that requires no sample transfer or pretreatment. In another embodiment, cotton-tipped electrochemical immunosensor plays dual function roles as sample collector as well as detector allowing the rapid, simple and low cost detection of the viruses without prior sample preparation.

CNF-modified screen printed carbon electrodes were used for the immunosensor fabrication on which the S or N antigens were immobilized after functionalization of the sensor surface by electrografting. Competitive assay was used for the detection of the S and N proteins showing excellent sensitivity and selectivity.

In one embodiment, a process of diagnosing a viral infection is performed using the steps of modifying an electrode using an electrode material to make a modified electrode; functionalizing the modified electrode by grafting a carboxy phenyl group to make a functional electrode; immobilizing a viral antigen on the functional electrode to make a viral antigen coated functional electrode; capping the viral antigen coated functional electrode with an layer of tip material to make a tipped electrochemical sensor; contacting the tipped electrochemical sensor with a mammalian body part which releases a mucous membrane secretion on the tipped electrochemical sensor; immersing the sample collected by the tipped electrochemical sensor into a tube containing a redox solution; and applying a voltage difference on the sample collected on the tipped electrochemical sensor in the tube containing redox to read a difference in a reduction peak current or charge transfer resistance using a square wave voltammetry or electrochemical impedance spectroscopy.

In another embodiment a method of diagnosing a viral infection is done by the following steps of modifying an electrode using carbon nanofiber to make a modified carbon electrode; grafting a carboxy phenyl group to make a functional carbon electrode by functionalizing the modified carbon electrode; coating a viral antigen on the functional carbon electrode to make a coated functional electrode; layering a cotton layer to make a cotton tipped electrochemical sensor on the viral antigen coated functional electrode with; collecting a sample from a mammalian body part infected by a virus which releases a mucous membrane secretion on the cotton tipped electrochemical sensor; immersing the sample collected cotton tipped electrochemical sensor into a tube containing a redox solution; applying a voltage difference on the sample collected cotton tipped electrochemical sensor in the tube containing redox to read a difference in a reduction peak current; and identifying the presence or absence of viral infection based on reduction peak current difference.

Other features will be apparent from the accompanying drawings and from the detailed description that follows.

BRIEF DESCRIPTION OF DRAWINGS

Example embodiments are illustrated by way of example and not limitation in the figures of the accompanying drawings, in which like references indicate similar elements and in which:

Figure 4:
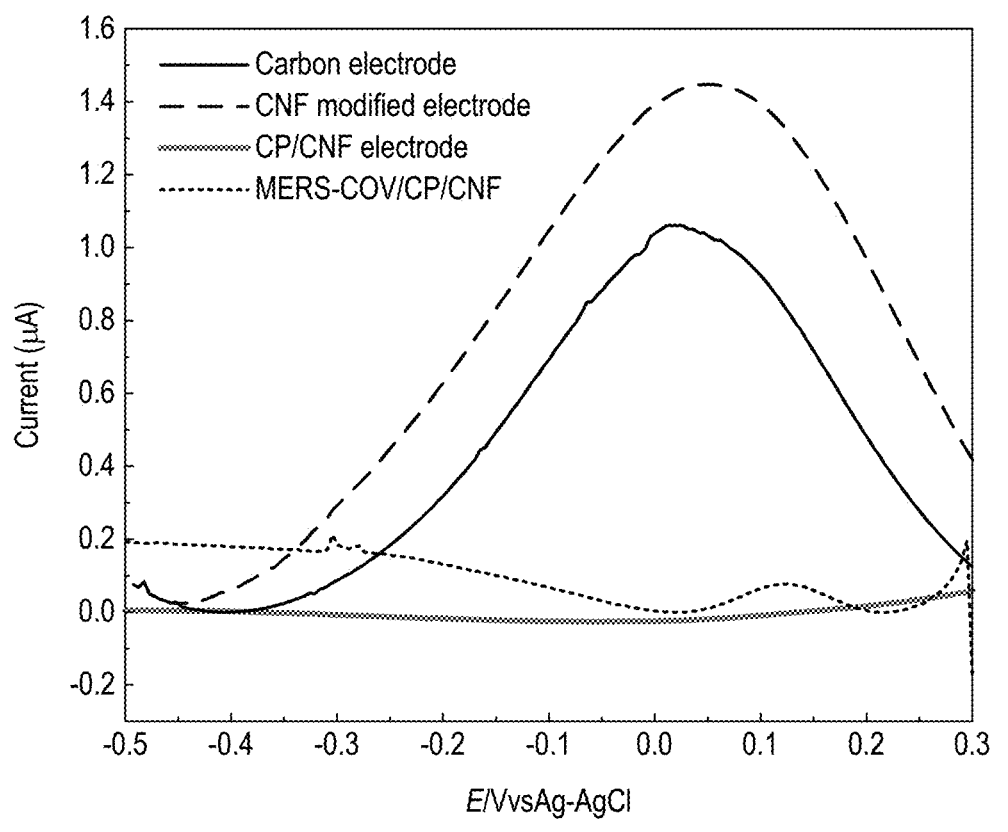

FIG. 4 shows the Square wave voltammograms of different electrodes.

Figures 1A, 1B, 1C:
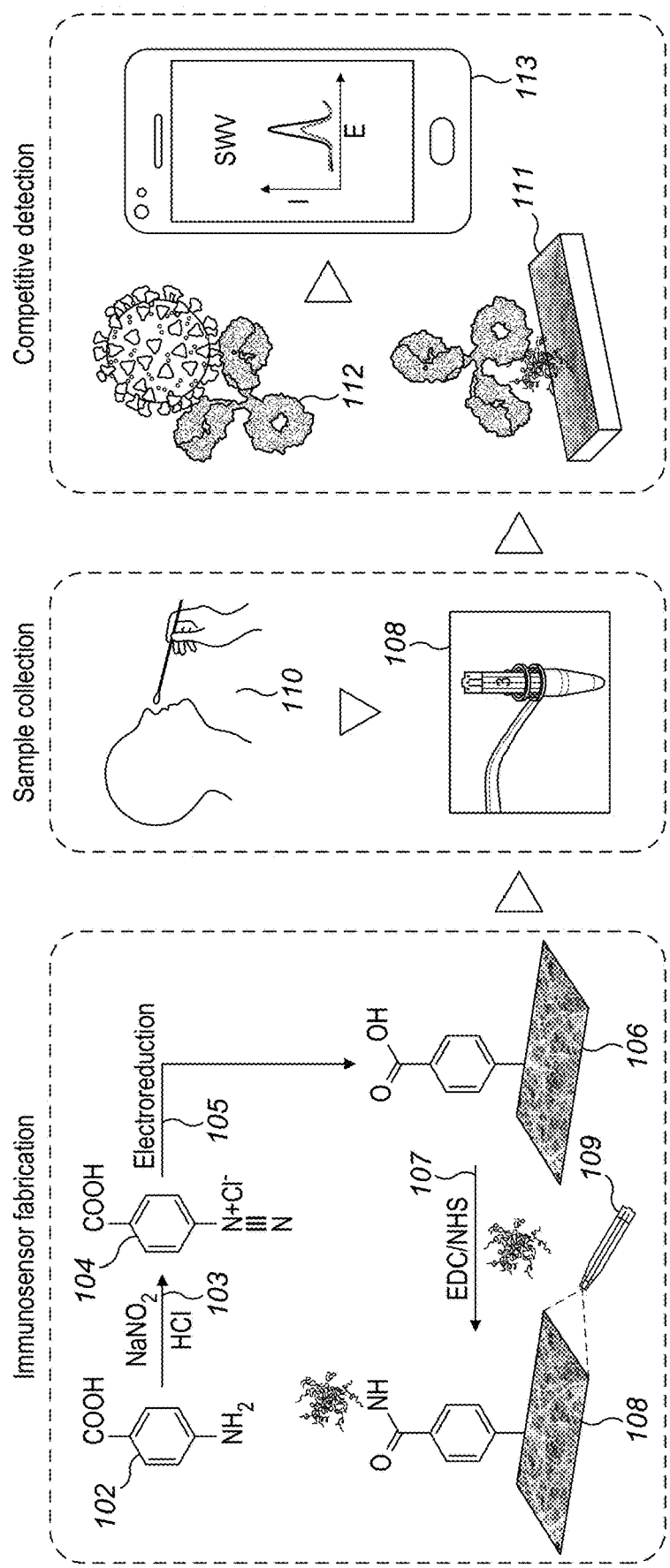
FIGS. 1A, 1B and 1C show steps of sensor fabrication, sample collection and competitive detection of corona virus.

Other features of the present embodiments will be apparent from the accompanying drawings and from the detailed description that follows.

DETAILED DISCUSSION

The instant disclosure describes a process and method for a rapid test for infectious disease such as COVID-19. This particular pandemic and other pandemics that spread and infect mammalians in a short duration. The severe acute respiratory syndrome coronavirus 2 (SARS-CoV-2) pandemic has led to an urgent need for low-cost and rapid diagnostic tools to enable the infection control and suppress the spread of the COVID 19 disease. The shorter the process and simpler the method it is easier for public health authorities to implement it. The instantly disclosed process and method for electrochemical immunosensor is a promising diagnostic tool for the direct rapid detection of the corona viruses that requires no sample transfer or pretreatment.

Our novel process and method is the combination of cotton fiber and electrochemical assay for the detection of SARS-CoV-2 and MERS-COV protein antigens. The cotton-tipped electrochemical immunosensor plays dual function roles as sample collector as well as detector allowing the rapid, simple and low cost detection of the viruses without prior sample preparation.

Materials and reagents: Potassium ferricyanide ($K_3Fe(CN)_6$), potassium ferrocyanide ($K_4Fe(CN)_6$), 4-aminobenzoic acid, hydrochloric acid, sodium nitrite, bovin serum albumin (BSA) and phosphate buffer saline (PBS) were obtained from Sigma (Ontario, Canada) (http://www.sigmaaldrich.com/canada-english.html). N-hydroxysuccinimide (NHS), 1-ethyl-3-(3-dimethylaminopropyl) carbodiimide hydrochloride (EDC) and PCR tubes were purchased from Fisher Scientific (Ontario, Canada). Carbon nanoFibers powder was obtained from Metrohm DropSens, Inc. (Asturias, Spain). Antigen of MERS-CoV (725 Spike protein 51) and the antigen of SARS-CoV-2 (Nucleocapsid protein (N protein)) and their antibodies were purchased from Sino Biological (Beijing, china) (https://www.sinobiological.com/). Influenza A antigen (N1H1) No. J8034 were purchased from biospacific (CA, USA) (https://www.biospacific.com/). HCoV antigen (HK41 N) and its antibody were obtained from Medix Biochemica (Finland). Sterile cotton was obtained from local pharmacy in Riyadh city. 1×PBS buffer, pH 5.5 was used for the preparation of EDC/NHS solution for the activation step. 1×PBS buffer, pH 7.4 was used for the preparation of the antigens and antibodies solutions and washing steps. The CNF solution was prepared by dispersion of 1 mg of the CNF powder in one ml of DMF with sonication for 30 min until obtaining a homogeneous solution. All the solutions were prepared using Milli-Q water.

Instrumentation: An Autolab potentiostat, PGSTAT302N from (Metrohm, Switzerland) was used to perform all the electrochemical measurements (the cyclic and square wave voltammetry). Disposable screen printed electrodes (PCR P01) adopted for PCR tubes were purchased from BioDevice Technology (Nomi, Japan). Each electrode consists of rectangle-shaped carbon working and counter electrodes and a central silver/silver chloride (Ag/AgCl) reference electrode. The electrical contacts are made of silver. The ends of the electrodes were designed to fit into the standard PCR tubes. The electrodes were connected to the potentiostat through a connector obtained from BioDevice Technology. The morphology of the CNF modified electrodes were examined via Scanning electron microscopy (SEM) measurements using an acceleration voltage of 5 kV, magnification=12000× and a working distance of 9.8 mm.

Modification of the carbon electrodes with carbon nanofibers: Drop casting method was used to modify the carbon working electrode of the screen printed chip. 0.5 μL of the CNF solution in DMF (1 mg/ml) was placed on the surface of the working electrodes. The electrodes were then left to dry at room temperature for at least 20 hours. Then, the electrodes were gently washed with water to remove the excess CNF and dried.

Method and process of functionalization of the carbon nanofiber-modified electrodes using electrografting: The CNF surface was then functionalized using electrografting of carboxyphenyl groups via the reduction of diazonium salt as previously reported on different carbon materials. Briefly, as shown in FIGS. 1A, 1B and 1C, 2 mM of 4-aminobenzoic acid solution (102) were mixed with 2 mM of sodium nitrite solution in 0.5 M HCl (103) with stirring for 10 min at room temperature to produce the diazonium salt (104). 100 μl of the diazonium solution was then added into a PCR tube in which the CNF electrode was immersed from one end and the other was connected to the potentiostat to perform electroreduction (105) using 2 cyclic voltammetry scans from +0.2 to −0.7 V at a scan rate of 50 mV s-1 to make the chips. The chips were then washed with water and dried. To confirm the success of the grafting step of the carboxyphenyl groups on the electrode surface, X-ray photoelectron spectroscopy (XPS) measurements were recorded for the CNF-modified electrodes before and after the electroreduction step.

Figure 2:
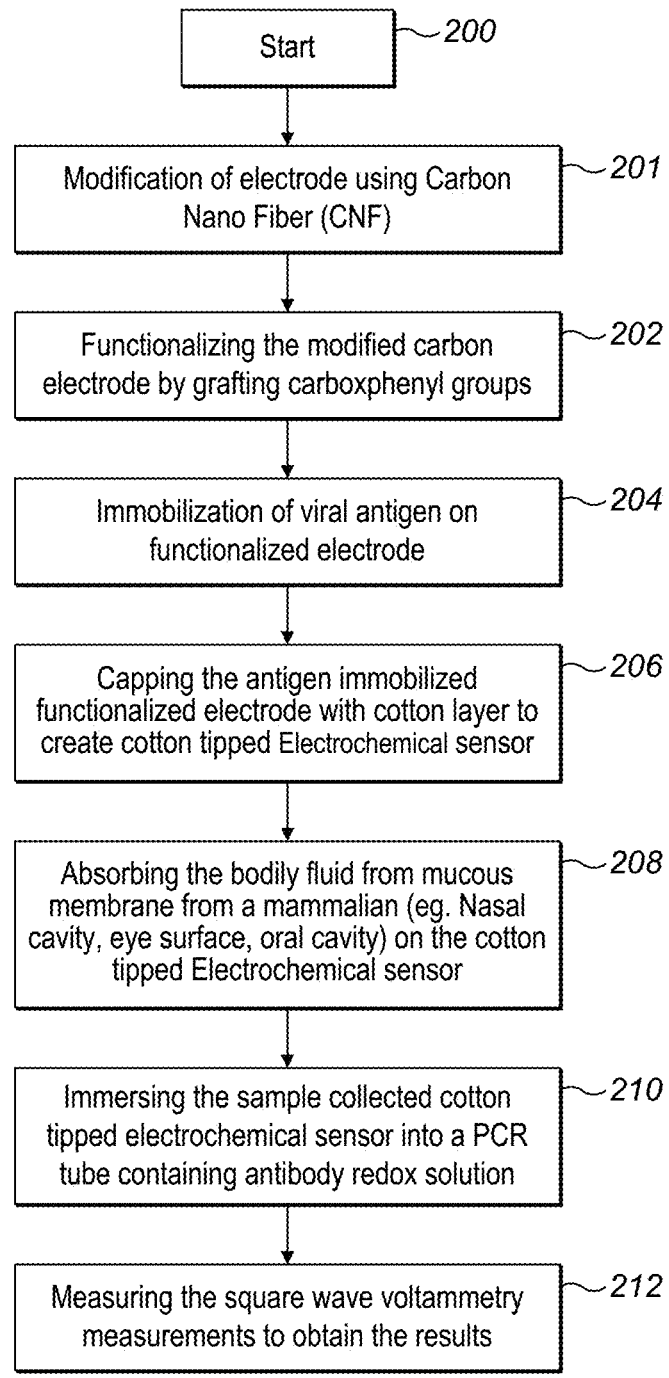
FIG. 2 shows a flow chart of the process and method of making and using the cotton tipped electrochemical sensor.
Figure 3A:
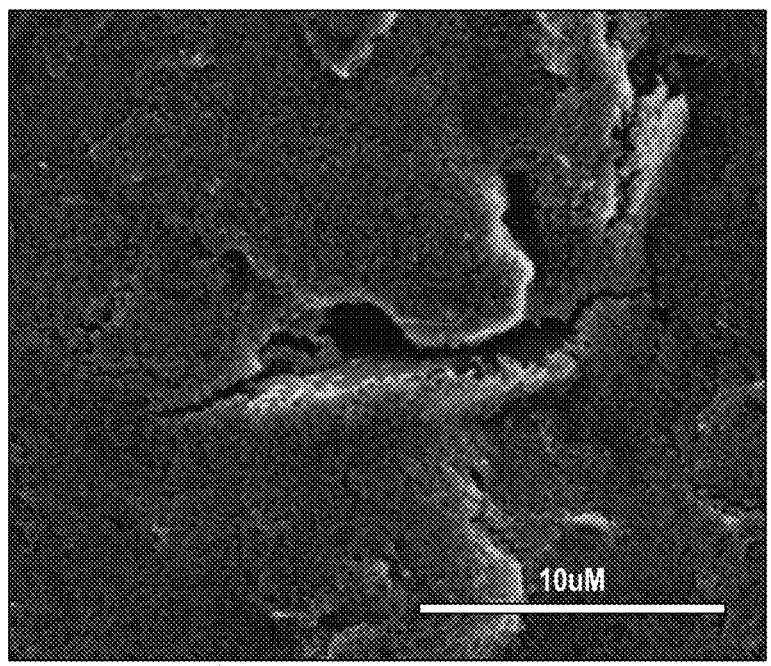
FIGS. 3A, 3B, 3C and 3D show scanning microscope images of the carbon screen printed electrodes and the carbon electrode after modification with carbon fibers and the The X-ray photoelectron spectroscopy C1s high resolution spectra of the modified electrodes before and after electro grafting.
Figure 3B:
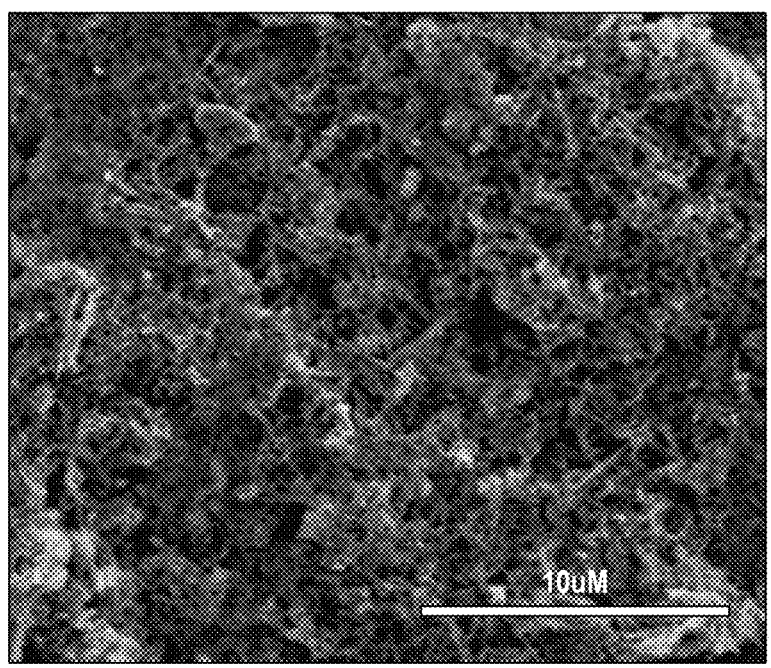
Figure 3C:
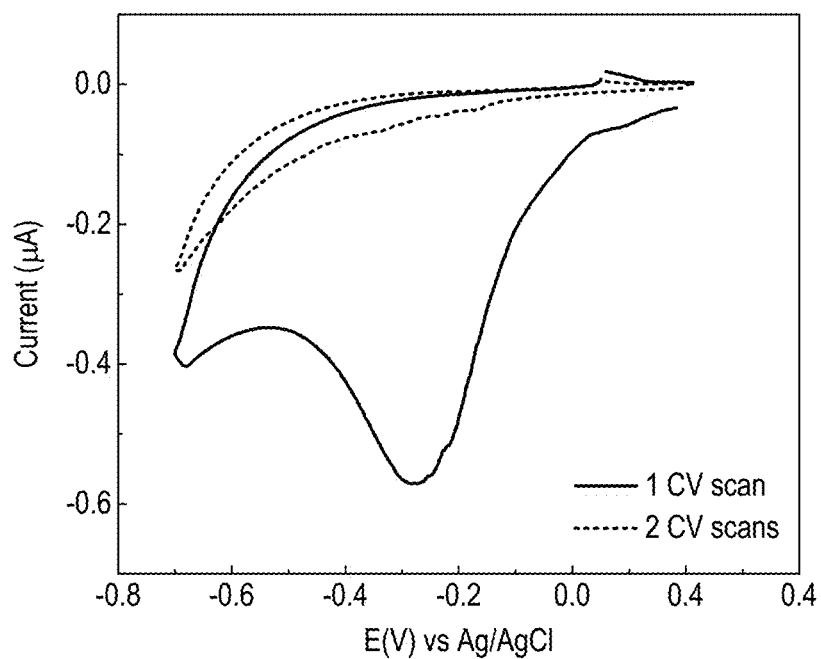
Figure 3D:
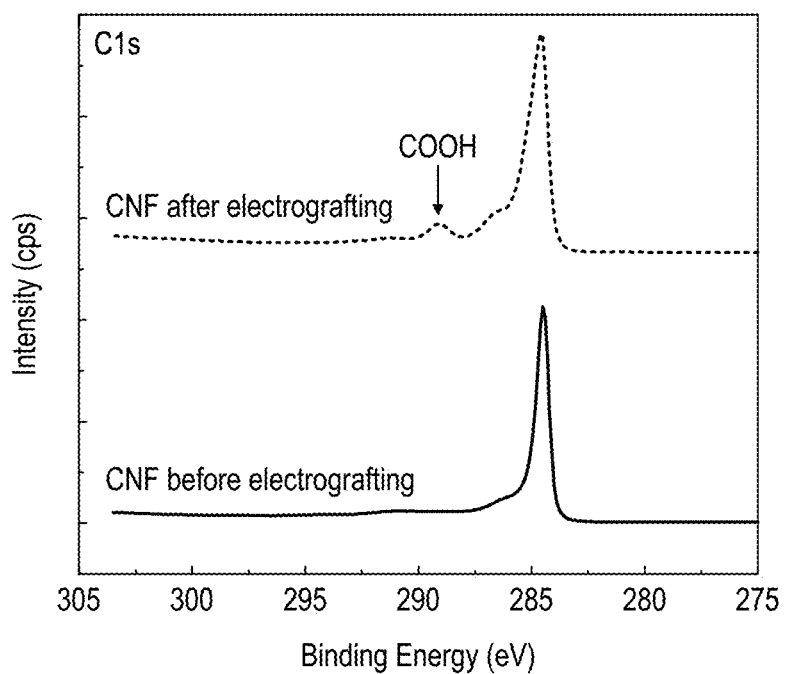
Figure 5A:
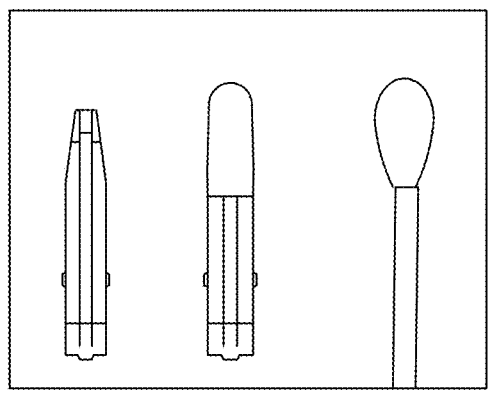
FIGS. 5A, 5B, 5C, 5D, 5E and 5F shows the various steps of using the cotton tipped electrochemical sensor.
Figure 5B:
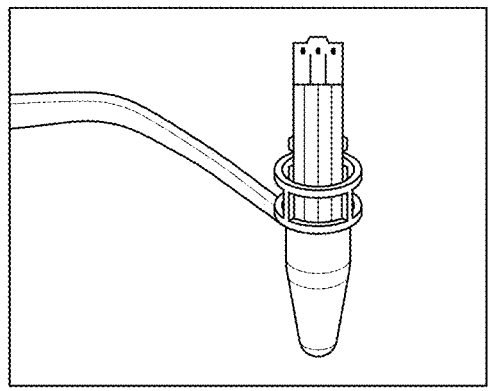
Figure 5C:
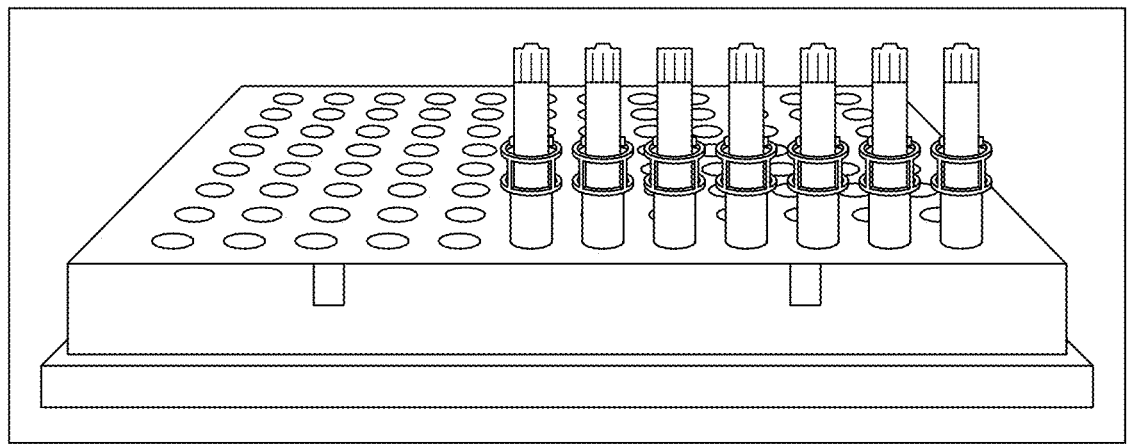
Figure 5D:
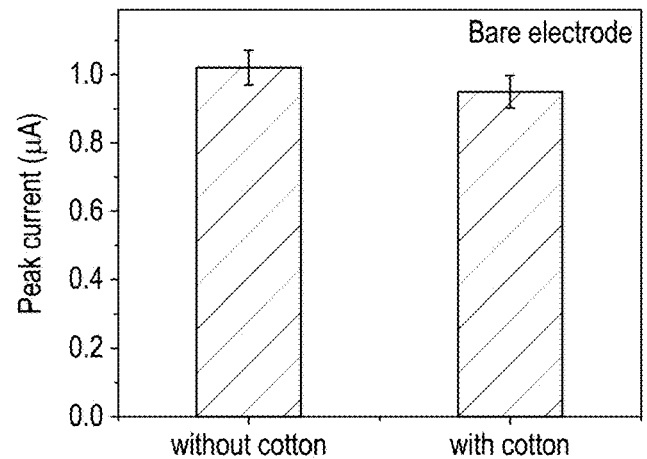
Figure 5E:
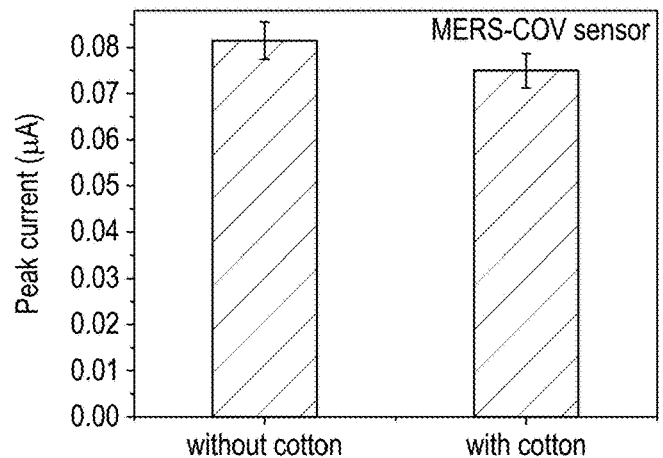
Figure 5F:
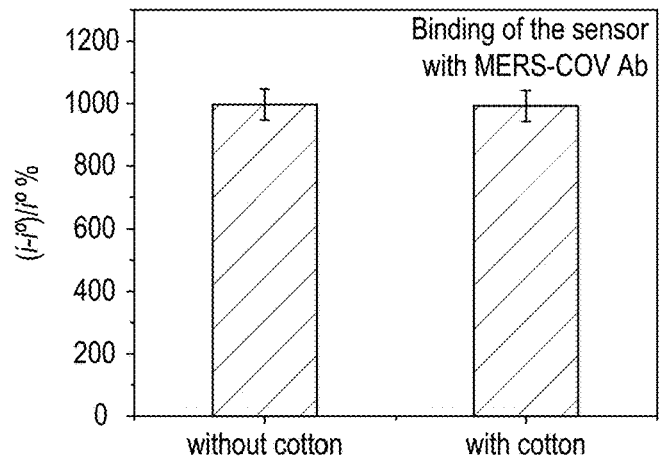
Figure 6A:
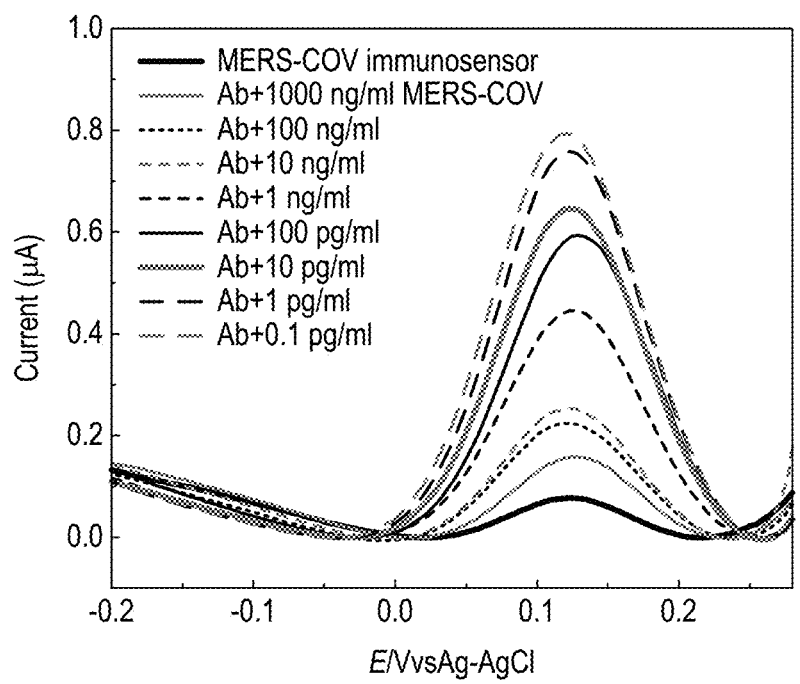
FIGS. 6A, 6B, 6C and 6D shows square wave voltammograms and detection curves of the MERS-CoV (A) and SARS-CoV-2 (C) immunosensors before and after binding with different concentrations of spike 51 and N antigens.
Figure 6B:
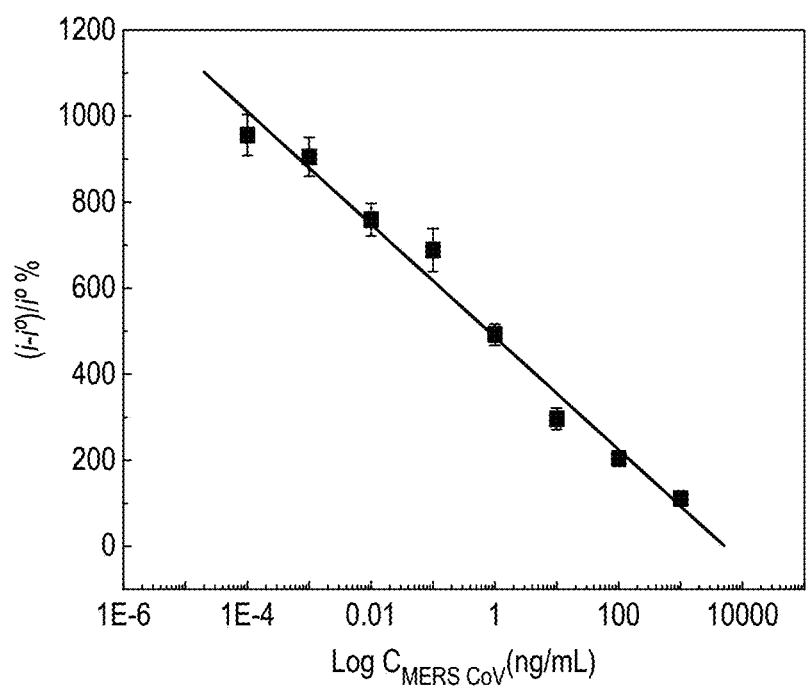
Figure 6C:
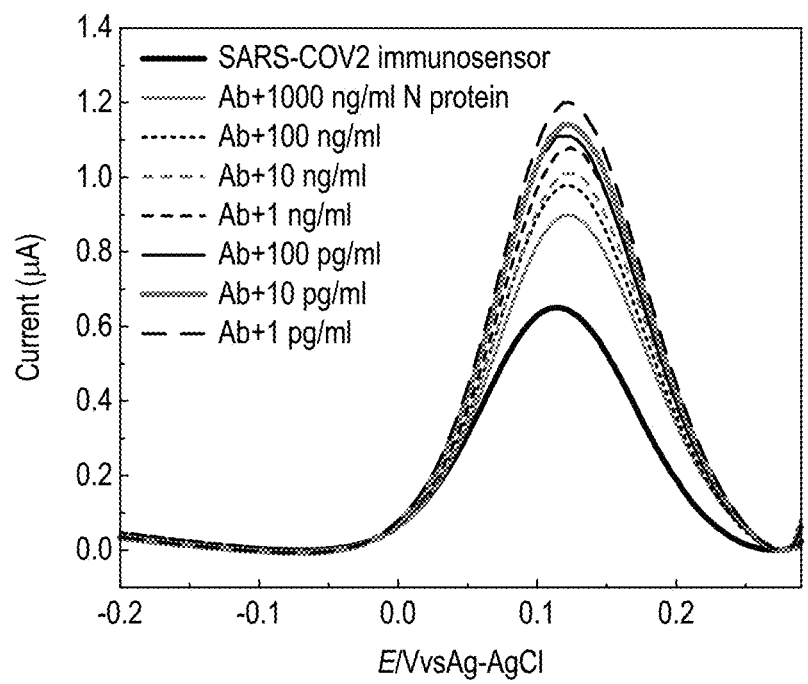
Figure 6D:
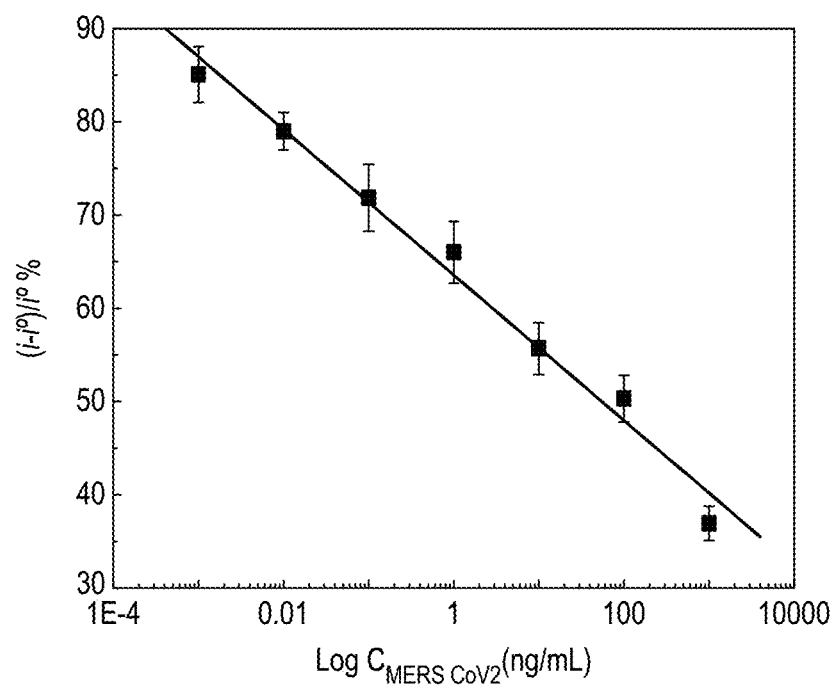

Immobilization of the virus antigens on the functionalized electrodes and preparation of the cotton-based electrochemical sensor was carried out in step 204 as also shown in FIG. 2. The carboxyphenyl-modified CNF electrodes (106) were incubated in PBS buffer, pH 5.5 containing 100 mM EDC and 20 mM NHS (107) for 1 hour at room temperature in order to activate the terminal carboxylic groups. After that, the electrodes were washed with PBS buffer pH 7.4 and incubated individually with 10 μg/ml of either the MERS-CoV or SARS CoV-2 antigens solutions (107) in PBS buffer, pH 7.4 for 3 hours in a water-saturated atmosphere at room temperature. Finally, the antigen-coated electrodes (108) were then rinsed using PBS buffer and incubated in a solution of 0.1% BSA in PBS buffer pH 7.4 for 30 min to block the free sites on the electrode surface.

After immobilizing the antigens, the cotton-tipped immunosensor (109) were prepared by covering the tapering end of the electrode containing the detection zone with a piece of cotton Fiber (30 mg) without scratching the sensor surface (FIG. 2, step 206). The prepared immunosensor can be used immediately for collecting the nasal sample (110) (FIG. 1B) (FIG. 2, step 208) or kept dry at 4° C. until further use (108).

Electrochemical competitive detection of MERS-CoV and SARS-CoV-2 on the cotton-based immunosensor: For the detection of the standard antigens solutions in PBS buffer, different concentrations (0.1 pg/ml to 1 μg/ml) of each antigen (the spike S1 or the N protein) was firstly mixed with 10 $\mu g \cdot mL^{-1}$ solution of the respective antibody in PBS buffer pH 7.4 off the chip in an Eppendorf Tube (112). Then, 100 μl of each mixture was added to a PCR tube in which the cotton-tipped immunosensor was then immersed and incubated for 20 min at room temperature (111). After the incubation, the immunosensor was taken out and placed in another PCR tube containing 100 μl PBS buffer and left for 1 min for washing. Then, the cotton electrode was placed on absorbing cotton pad to remove the excess washing solution. Finally, the immunosensor was immersed into a PCR tube containing 10 mM of the redox solution (ferro/ferricyanide) in PBS buffer pH 7.4 to maintain all electrodes in contact with the solution during the SWV measurements (FIG. 2, step 210). The electrochemical sensor response was calculated as $(i-i^o)/i^o$% where, i is the reduction peak current of the electrodes after incubation with the mixture of the antigen and antibody solution and $i^o$ is the original peak current of the immunosensor before incubation.

Electrochemical measurements: The Square wave voltammetry measurements (SWV) were recorded in 10 mM 1:1 ferro/ferricyanide solution in 10 mM PBS buffer pH 7.4 (FIG. 2, step 212). The scanning potential range of the SWV is from 0.3 to −0.5 V at step potential of −5 mV, amplitude of 20 mV and frequency of 25 Hz. Base-line corrections were performed for all the SWV curves. The cyclic voltammetry measurements (C) for the diazonium electroreduction was performed at a scan rate of 50 mV s-1 by CV scanning from +0.2 to −0.7 V (113).

Cross reactivity testing of the immunosensor with other antigens: In order to study the selectivity of the MERS-CoV and SARS-CoV-2 immunosensor towards their antigens, the immunosensor were tested against Flu A and HCoV antigens. The test was performed by mixing 10 μl of MERS-CoV antibody (10 μg/ml) with 10 μl of Flu A or HCoV antigen solution (1 ng/ml) and 10 μl of SARS-CoV-2 antibody (10 μg/ml) with 10 μl of Flu A or HCoV antigens (1 ng/ml). Then, the mixtures were incubated with each immunosensor for 20 min and then washed. The sensor response in each case was evaluated as described above.

Testing of the immunosensor on spiked nasal fluid: The cotton-tipped immunosensor were used to collect nasal fluid from healthy volunteer. Then the immunosensor was immersed in PCR tube containing 50 μl of 10 μg/ml solution of spike S1 antibody spiked with 50 μl of 0.001 or 100 ng/ml of the spike S1 protein solution in PBS buffer pH 7.4. The immunosensor were incubated for 20 min then washed and measured by SWV as described above.

The method and process is described in FIG. 2. The start 200 is modification of the electrode using carbon nanofiber (CNF) (201). The entire process and method is done to create cotton tipped electrochemical sensor, method of using it to collect sample and finally measuring the results using square wave voltammetry and reading the measurements to detect the said virus. The electrode material can be one of a carbon nanofiber, carbon nanotubes, graphene or any other carbon nanomaterial. And the tip/cover material can be cotton or other synthetic fiber such as nylon, Rayon, polyurethane foam, and Polyester. And the electrochemical measurements can be done using square wave voltammetry or electrochemical impedance spectroscopy.

A process to functionalize the modified carbon electrode is done by grafting carboxyphenyl groups to the surface (202). FIG. 1 A describes this method and process in detail. Immobilization of viral antigen on the functionalized electrode is described in FIG. 1A step 109. Step 206 describes capping the antigen immobilized functionalized electrode with cotton layer to create cotton tipped electrochemical sensor or any other layer that can absorb the sample and yet be electro sensitive is important.

Characterization of the carbon nanofiber-modified electrodes before and after the electrografting of carboxyphenyl moieties: In this work, we used screen printed carbon electrodes for the sensor fabrication. Commercially available CNF powder in DMF was used to modify the carbon working electrodes. Scanning electron microscopy (SEM)

was used to characterize the morphology of the carbon working electrodes as well as the CNF-modified electrodes. As shown in FIGS. 3A and 3B, the SEM images of the carbon and CNF-modified electrodes exhibited different morphologies. The carbon electrode showed a typical multilayered graphitic structure, whereas, the CNF electrodes exhibited a densely packed layer of CNF rods indicating higher surface area of the CNF electrodes compared with the unmodified carbon electrode.

The CNF electrodes were then functionalized by electrografting of the carboxyphenyl layer in the electrode surface. The electrografting was achieved via electroreduction of carboxyphenyl diazonium salt by CV. As shown in FIG. 3C, the first CV scan showed a single irreversible cathodic peak at 0.3 V, characteristic for the reduction of diazonium salt via one electron transfer process which led to the removal of nitrogen molecule and the formation of aryl radical that form a covalent bond with the CNF surface. However, in the second CV scan, the reduction peak was almost disappeared likely due to the complete coverage of the CNF electrode surface with the carboxyphenyl layer which retarded the electron transfer process. Further CV scans will lead to a buildup of multilayers which will negatively impact the biosensor performance as previously reported. Thus, only 2 CV scans were performed for the electrografting step to ensure monolayer formation of the carboxyphenyl moieties.

XPS was then used to analyze the CNF electrode surface before and after the electrografting step using CV. FIG. 3D shows the XPS C1s high resolution spectra of the electrode before and after functionalization. A new peak was observed clearly at 288.8 eV after the electrografting step compared with the spectra of the unmodified CNF electrode which confirms the successful attachment of the carboxyl groups on the CNF surface.

Square wave voltammetry characterization of the stepwise fabrication process of the biosensor: To characterize the fabrication steps of the immunosensor, SWVs were recorded at different steps in ferro/ferricyande solution. FIG. 4 shows the SWV reduction peaks of the redox couple at the bare carbon electrode, the CNF-modified electrode, the carboxyphenyl-modified electrode and after the immobilization of the spike S1 protein. As shown in the figure, an enhancement of the reduction peak current was observed when the electrode was modified with CNF compared to the bare carbon electrode. This is attributed to the increase in the electrochemical surface area of the electrode because of the CNF material. However, after the electroreduction step of the diazonium salt on the CNF electrode, the SWV reduction signal of the redox couple was almost disappeared due to the formation of the carboxyphenyl layer on the electrode surface. This has led to the passivation of the electrode and retardation of the electron transfer because of the aromatic layer. Moreover, the negatively charged carboxyl groups repelled the redox anion from the surface leading to a decrease in the reduction current. However, the immobilization of the virus protein antigen on the carboxyphenyl-modified electrode after activation with EDC/NHS led to an increase in the reduction peak current. This is likely attributed to the shielding of the negatively charged carboxylic groups on the CNF surface with the antigens.

Effect of the cotton coating on the electrochemical signal of the electrode: The goal of this work is to develop a cotton-tipped electrochemical immunosensor which can perform both the sample collection as well as the detection. After the immobilization of the protein antigen on the CNF electrode, the electrodes were blocked with BSA solution and left to dry at room temperature. Then, a piece of cotton Fiber was then coated on the detection zone of the electrode as shown in FIG. 5A which mimics the standard Q-Tip. The cotton was used because of its high absorbing capability which allows the collection of the nasal samples by swabbing. The incubation of the sensor with the antibody solution as well as the measuring redox solution is done in PCR tubes as shown in FIGS. 5B and 5C.

Investigation was carried out to find out if the coating of the electrode with the cotton fiber impacts the electrochemical signal. FIG. 5D shows the SWV reduction peak current of the bare electrode before and after coating with the cotton in the redox solution. Non-significant change (less than 5%) in the electrochemical signal was observed after coating the carbon electrode with the cotton likely due to the high absorbing properties of the cotton Fiber. The cotton fiber was able to absorb the redox solution by capillary action and transports it to the electrode surface which remains in contact with the solution during the measurements. FIG. 5E shows the reduction peak current at MERS-CoV immunosensor (the spike S1 modified electrode after blocking with BSA) before and after coating with the cotton. The change in the peak current was less than 5% indicating that there was no significant effect on the electrochemical signal of the sensor due to the coating with the cotton. It was also important to assess the effect of cotton coating on the biosensor response due to the binding of the antigen on the sensor surface with the antibody in the solution. For this purpose, the reduction current of the uncoated and cotton coated immunosensor were detected in the redox solution. Then the two immunosensor were incubated in 1 ng/ml solution of antibody in two PCR tubes. After washing, the electrodes were measured in the redox solution and the sensor response in was evaluated as the percentage change in the reduction peak current in each case. As shown in FIG. 5F, the cotton-tipped biosensor response was almost similar to the uncoated immunosensor. These results imply that the cotton-tipped electrochemical sensor can be used as an effective platform with dual function as a sample collector and detection tool.

Competitive electrochemical detection of MERS-CoV and SARS-CoV-2 on the immunosensor: The detection on the immunosensor was achieved via competitive assay where a fixed concentration of antibody is mixed in the solution with different concentrations (0.1 pg/ml to 1 μg/ml) of the spike S1 or N protein antigen solution and then incubated on the immunosensor surface. A competition between the immobilized and the free antigen to bind the free antibody in the solution is realized. The higher the concentration of free antigen, the smaller the amount of antibody available to bind to the antigen on the electrode surface. The binding of the antibody to the antigen on the immunosensor causes an increase in the reduction peak current of the ferro/ferricyanide redox couple. This could be attributed to the binding with the positively charged antibodies which attract the redox anions leading to an enhancement of the reduction current.

FIG. 6A shows the SWVs of the MERS-CoV immunosensor upon incubation with different concentrations of spike S1 protein mixed with 10 μg/ml of the antibody solution. When the concentration of the spike S1 protein was high, the increase in the SWV peak current was low and vice versa. Similarly, the SWVs of the SARS-CoV-2 immunosensor upon incubation with different concentrations of nucleocapsid protein mixed with 10 μg/ml of the antibody solution are shown in FIG. 6C. The calibration plots of the MERS-CoV and SARS-CoV-2 immunosensor are shown in FIGS. 6B and 6D, respectively. The calibration plot is obtained by plotting the biosensor response (the percentage increase in the peak current; (i−i°)/i°%) versus the logarithm of the antigen concentration. Good linear relationship was obtained for the concentration ranges from 0.1 pg/ml to 1000 ng·mL-1 and 1 to 1000 ng·mL-1 for MERS-CoV and SARS-CoV-2, respectively. The linear regression equations of the two straight lines were: (i−io)/io %=477.8+−124.6 log C (ng/ml), R=0.992 for MERS-CoV and (i−i°)/i°%=63.6+−7.8 log C (ng/ml), R=0.991 for SARS-CoV-2. The limits of detection (LODs) were calculated to be 0.8 and 0.09 pg/ml for SARS-CoV-2 and MERS-CoV, respectively indicating excellent sensitivity of the immunosensor. These LODs are much lower than other reported immunoassays such as ELISA (LOD of ELISA is 0.4 ng/ml and 1 ng/ml for SARS-CoV-2 and MERS-CoV, respectively). All the experiments were done in triplicates and the standards deviations of the measurements were ranging from 2.5 to 5.5% indicating excellent reproducibility of the two electrochemical immunosensor.

Figure 7A:
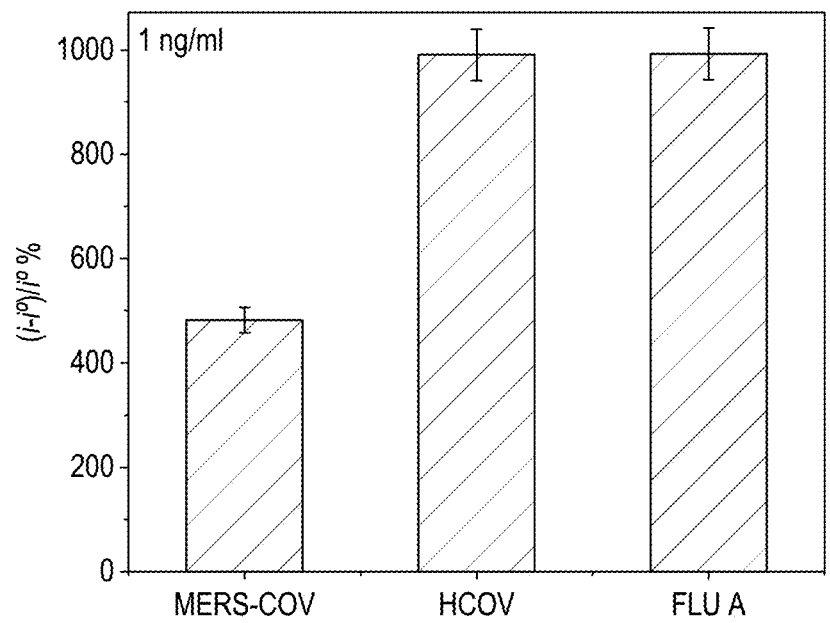
FIGS. 7A and 7B shows the MERS-CoV and SARS-CoV-2 biosensors response towards the binding with Spike 51, N, Flu A and HCoV antigens.
Figure 7B:
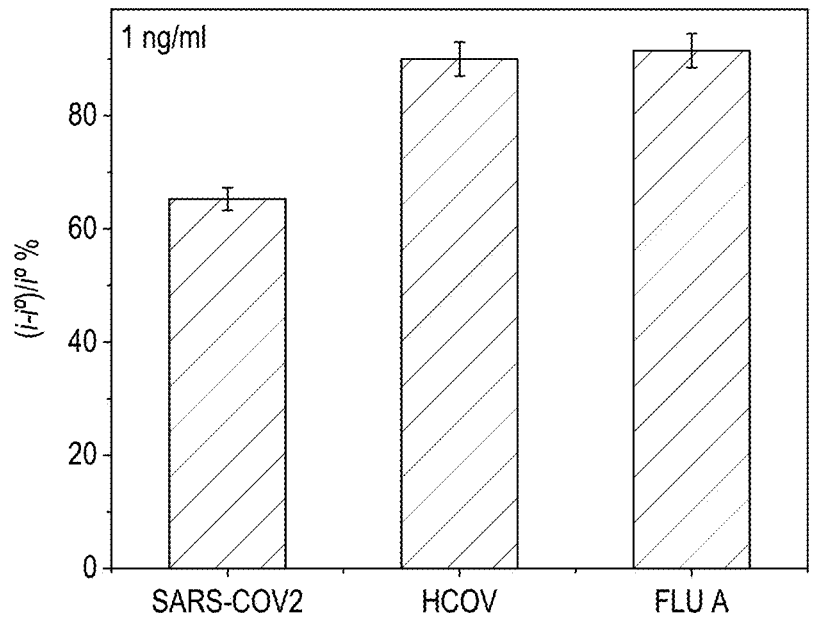

Cross reactivity of the MERS-CoV and SARS-CoV immunosensor with other virus antigens: In order to confirm the selectivity of our immunosensor to the Spike S1 and nucleocapsid proteins, the immunosensor were tested against other virus antigens such as Flu A and HCoV. FIGS. 7A and 7B show the MERS-CoV and SARS-CoV immunosensor responses against Spike S1 and nucleocapsid proteins as well as HCoV and Flu A. As shown in the figure, significant difference between the response of each immunosensor towards its specific and nonspecific antigens. Higher sensor response was obtained in the case of the nonspecific antigens because there were no binding in the solution and thus, the maximum amount of antibody was free to bind to the electrode whereas, lower response was obtained when the specific antigen was used. These results indicate high selectivity of the MERS-CoV and SARS-CoV electrochemical immunosensor.

Application of the cotton-tipped immunosensor in spiked nasal samples: To investigate the practical applicability of the developed cotton-tipped electrochemical immunosensor for the detection of the virus in the nasal fluid, the sensor was used to collect the nasal fluid from healthy volunteer and then subjected to the electrochemical measurements as described in the experimental section. Table 1 shows very good recovery percentages (91 to 95.5%) of the spike S1 protein on the MERS CoV cotton immunosensor. This indicates the success of the cotton immunosensor to collect as well as detect the virus protein with high accuracy and without significant interference from the other component of the nasal fluid.

TABLE 1 the real sample application of the MERS-CoV immunosensor in spiked nasal samples (n = 3) showing the recovery percentages.

| Spiked MERS-CoV ng/mL | Recovery % | RSD % |
|---|---|---|
| 0.001 | 95.5 | 5.2 |
| 100 | 91 | 6.0 |

What is claimed is:

1. A process to diagnose a viral infection, comprising:
    modifying an electrode using an electrode material to make a modified electrode;
    functionalizing the modified electrode by grafting a carboxy phenyl group to make a functional electrode;
    immobilizing a viral antigen on the functional electrode to make a viral antigen coated functional electrode;
    capping the viral antigen coated functional electrode with an layer of tip material to make a tipped electrochemical sensor; wherein the layer of tip material is one of a cotton, nylon, rayon, polyurethane foam or polyester;
    contacting the tipped electrochemical sensor with a mammalian body part which releases a mucous membrane secretion on the tipped electrochemical sensor;
    immersing the sample collected by the tipped electrochemical sensor into a tube containing antibody solution and a redox solution; and
    applying a voltage difference on the sample collected on the tipped electrochemical sensor in the tube containing redox to read a difference in a reduction peak current using a square wave voltammetry or a charge transfer resistance using electrochemical impedance spectroscopy using Smartphone.

2. The process of claim 1, wherein the reduction peak current is done using the square wave voltammetry.

3. The process of claim 1, wherein the charge transfer resistance is done using the electrochemical impedance spectroscopy.

4. The process of claim 1, wherein the mammalian body part is one of a nasal cavity, oral cavity or corneal surface.

5. The process of claim 1, wherein the layer of tip material is a cotton.

6. The process of claim 1, wherein the electrode material is one of a carbon nanofiber, carbon nanotubes, graphene or any other carbon nanomaterial.

7. The process of claim 6, wherein the electrode material is the carbon nanofiber.

8. The process of claim 1, wherein the viral infection is due to a Corona Virus.

9. A process to diagnose a viral infection, comprising:
    modifying an electrode using carbon nanofiber to make a modified carbon electrode;
    functionalizing the modified carbon electrode by grafting a carboxy phenyl group to make a functional carbon electrode;
    immobilizing a viral antigen on the functional carbon electrode to make a viral antigen coated functional electrode;
    capping the viral antigen coated functional electrode with a cotton layer to make a cotton tipped electrochemical sensor;
    contacting the cotton tipped electrochemical sensor to a mammalian body part which releases a mucous membrane secretion on the cotton tipped electrochemical sensor;
    immersing the sample collected cotton tipped electrochemical sensor into a tube containing antibody and a redox solution; and
    applying a voltage difference on the sample collected cotton tipped electrochemical sensor in the tube containing redox to read a difference in a reduction peak current.

10. The process of claim 1, wherein the viral infection is due to a Corona Virus.

11. A method of diagnosing a viral infection, comprising;
    modifying an electrode using carbon nanofiber to make a modified carbon electrode;
    grafting a carboxy phenyl group to make a functional carbon electrode by functionalizing the modified carbon electrode;
    coating a viral antigen on the functional carbon electrode to make a coated functional electrode;

layering a cotton layer to make a cotton tipped electrochemical sensor on the viral antigen coated functional electrode with;

collecting a sample from a mammalian body part infected by a virus which releases a mucous membrane secretion on the cotton tipped electrochemical sensor;

immersing the sample collected cotton tipped electrochemical sensor into a tube containing antibody and redox solution;

applying a voltage difference on the sample collected on the cotton tipped electrochemical sensor in the tube containing redox to read a difference in a reduction peak current; and identifying the presence or absence of viral infection based on current difference.

12. The method of claim 11, wherein the viral infection is due to a Corona Virus.

13. The method of claim 11, wherein the reduction peak current is done using the square wave voltammetry.

* * * * *